(12) United States Patent
Kragh et al.

(10) Patent No.: US 6,218,508 B1
(45) Date of Patent: Apr. 17, 2001

(54) ANTI-MICROBIAL PROTEINS

(75) Inventors: Karsten Matthias Kragh, Viby; Jørn Dalgaard Mikkelsen, Hvidovre; Klaus Kristian Nielsen, Copenhagen, all of (DK)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/632,511

(22) PCT Filed: Oct. 20, 1994

(86) PCT No.: PCT/EP94/03449

§ 371 Date: Apr. 17, 1996

§ 102(e) Date: Apr. 17, 1996

(87) PCT Pub. No.: WO95/11306

PCT Pub. Date: Apr. 27, 1995

(30) Foreign Application Priority Data

Oct. 21, 1993 (GB) .................................................. 9321714

(51) Int. Cl.⁷ ............................. C07K 5/00; C07K 14/00; C07K 1/14
(52) U.S. Cl. ........................ 530/344; 435/69.1; 435/69.2; 435/375; 530/300; 530/324; 530/370
(58) Field of Search .................................. 435/69.1, 69.2, 435/375; 514/2; 530/300, 324, 344, 370

(56) References Cited

U.S. PATENT DOCUMENTS 5,514,779 * 5/1996 Broekaert et al. .................... 530/379
5,597,801 * 1/1997 Broekaert et al. .................... 514/12

FOREIGN PATENT DOCUMENTS

9411511 * 5/1994 (WO) .

* cited by examiner

*Primary Examiner*—John S. Brusca
*Assistant Examiner*—Sean McGarry
(74) *Attorney, Agent, or Firm*—Thomas Hoxie

(57) ABSTRACT

An anti-microbial protein comprising a peptide having the amino acid sequence: $AA_1$-$AA_2$-$AA_3$-Cys-$AA_5$-$AA_6$-$AA_7$-$AA_8$-$AA_9$-CYS-$AA_{11}$-$AA_{12}$-$AA_{13}$-$AA_{14}$-Cys-Cys-$AA_{17}$-$AA_{18}$-$AA_{19}$-$AA_{20}$-$AA_{21}$-Cys-$AA_{23}$-$AA_{24}$-$AA_{25}$-$AA_{26}$-$AA_{27}$-$AA_{28}$-Cys-$AA_{30}$. An anti-microbial protein having the sequence depicted in any one of SEQ ID Nos 1–3. Recombinant DNA encoding such proteins. A vector comprising such DNA which is expressible in plants and which is linked to a plant operable promoter and terminator. Plants transformed with such recombinant DNA; the progeny of such plants which contain the DNA stably incorporated and hereditable in a Mendelian manner, and/or the seeds of such plants or such progeny.

12 Claims, 8 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 91 amino acids
      (B) TYPE: amino acid
      (C) STRANDEDNESS: single
      (D) TOPOLOGY: unknown (ii) MOLECULE TYPE: protein (iii) HYPOTHETICAL: NO (iii) ANTI-SENSE: NO (vi) ORIGINAL SOURCE:
      (A) ORGANISM: Beta vulgaris (xi) SEQUENCE DESCRIPTION: SEQ ID NO:1:

```
Ile Thr Cys Gly Leu Val Ala Ser Lys Leu Ala Pro Cys Ile Gly Tyr
1               5                   10                  15

Leu Gln Gly Ala Pro Gly Pro Ser Ala Gly Cys Cys Gly Gly Ile Lys
                20                  25                  30

Gly Leu Asn Ser Ala Ala Ala Ser Pro Ala Asp Arg Lys Thr Ala Cys
            35                  40                  45

Thr Cys Leu Lys Ser Ala Ala Thr Ser Ile Lys Gly Ile Asn Tyr Gly
        50                  55                  60

Lys Ala Ala Ser Leu Pro Arg Gln Cys Gly Val Ser Val Pro Tyr Ala
65                  70                  75                  80

Ile Ser Pro Asn Thr Asn Cys Asn Ala Ile His
                85                  90
```

(2) INFORMATION FOR SEQ ID NO:2:

(i) SEQUENCE CHARACTERISTICS:
      (A) LENGTH: 91 amino acids
      (B) TYPE: amino acid
      (C) STRANDEDNESS: single
      (D) TOPOLOGY: unknown (ii) MOLECULE TYPE: protein (iii) HYPOTHETICAL: NO (iii) ANTI-SENSE: NO (vi) ORIGINAL SOURCE:
      (A) ORGANISM: Beta vulgaris (xi) SEQUENCE DESCRIPTION: SEQ ID NO:2:

```
Ile Thr Cys Gly Leu Val Ala Ser Lys Leu Ala Pro Cys Ile Gly Tyr
1               5                   10                  15

Leu Gln Gly Ala Pro Gly Pro Ser Ala Gly Cys Cys Gly Gly Ile Lys
                20                  25                  30

Gly Leu Asn Ser Ala Ala Ala Ser Pro Ala Asp Arg Lys Thr Ala Cys
            35                  40                  45

Thr Cys Leu Lys Ser Ala Ala Thr Ser Met Lys Gly Ile Asn Tyr Gly
        50                  55                  60

Lys Ala Ala Ser Leu Pro Arg Gln Cys Gly Val Ser Ile Pro Tyr Ala
65                  70                  75                  80
```

Ile Ser Pro Asn Thr Asn Cys Asn Ala Ile His
                85                  90

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: protein (iii) HYPOTHETICAL: NO (iii) ANTI-SENSE: NO (vi) ORIGINAL SOURCE:
         (A) ORGANISM: Beta vulgaris (xi) SEQUENCE DESCRIPTION: SEQ ID NO:3:

Ser Gly Glu Cys Asn Met Tyr Gly Arg Cys Pro Pro Gly Tyr Cys Cys
1               5                   10                  15

Ser Lys Phe Gly Tyr Cys Gly Val Gly Arg Ala Tyr Cys Gly
                20                  25                  30

(2) INFORMATION FOR SEQ ID NO:4:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: protein (iii) HYPOTHETICAL: NO (iii) ANTI-SENSE: NO (vi) ORIGINAL SOURCE:
         (A) ORGANISM: Beta vulgaris (xi) SEQUENCE DESCRIPTION: SEQ ID NO:4:

Ala Ile Cys Lys Lys Pro Ser Lys Phe Phe Lys Gly Ala Cys Gly Arg
1               5                   10                  15

Asp Ala Asp Cys Glu Lys Ala Cys Asp Gln Glu Asn Trp Pro Gly Gly
                20                  25                  30

Val Cys Val Pro Phe Leu Arg Cys Glu Cys Gln Arg Ser Cys
                35                  40                  45

(2) INFORMATION FOR SEQ ID NO:5:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: protein (iii) HYPOTHETICAL: NO (iii) ANTI-SENSE: NO (vi) ORIGINAL SOURCE:
         (A) ORGANISM: Beta vulgaris (xi) SEQUENCE DESCRIPTION: SEQ ID NO:5:

```
Ala Thr Cys Arg Lys Pro Ser Met Tyr Phe Ser Gly Ala Cys Phe Ser
1               5                   10                  15

Asp Thr Asn Cys Gln Lys Ala Cys Asn Arg Glu Asp Trp Pro Asn Gly
                20                  25                  30

Lys Cys Leu Val Gly Phe Lys Cys Glu Cys Gln Arg Pro Cys
                35                  40                  45
```

(2) INFORMATION FOR SEQ ID NO:6:

(i) SEQUENCE CHARACTERISTICS:
        (A) LENGTH: 32 amino acids
        (B) TYPE: amino acid
        (C) STRANDEDNESS: single
        (D) TOPOLOGY: unknown (ii) MOLECULE TYPE: protein (iii) HYPOTHETICAL: NO (iii) ANTI-SENSE: NO (vi) ORIGINAL SOURCE:
        (A) ORGANISM: Beta vulgaris (xi) SEQUENCE DESCRIPTION: SEQ ID NO:6:

```
Arg Cys Ile Pro Cys Gly Gln Asp Cys Ile Ser Ser Arg Asn Cys Cys
1               5                   10                  15

Ser Pro Cys Lys Cys Asn Phe Gly Pro Pro Val Pro Arg Cys Thr Asn
                20                  25                  30
```

(2) INFORMATION FOR SEQ ID NO:7:

(i) SEQUENCE CHARACTERISTICS:
        (A) LENGTH: 550 base pairs
        (B) TYPE: nucleic acid
        (C) STRANDEDNESS: double
        (D) TOPOLOGY: unknown (iii) HYPOTHETICAL: NO (iii) ANTI-SENSE: NO (vi) ORIGINAL SOURCE:
        (A) ORGANISM: Beta vulgaris (ix) FEATURE:
        (A) NAME/KEY: CDS
        (B) LOCATION: 66..293

(xi) SEQUENCE DESCRIPTION: SEQ ID NO:7:

```
ACTCAACAAA TTCAGAAAAA AACAGAAGCA AAAAAGTTT ATTGAAAGAG TAAGTTGAGG      60

TGAAA ATG ATG ATG AAA AGC TTT GTG ATA GTT ATG TTG GTC ATG TCC ATG   107
      Met Met Met Lys Ser Phe Val Ile Val Met Leu Val Met Ser Met
          1               5                   10

ATG GTG GCT ACA TCT ATG GCA AGT GGT GAA TGC AAT ATG TAT GGT CGA    155
Met Val Ala Thr Ser Met Ala Ser Gly Glu Cys Asn Met Tyr Gly Arg
15                  20                  25                  30

TGC CCC CCA GGG TAT TGT TGT AGC AAG TTT GGC TAC TGT GGT GTC GGA    203
Cys Pro Pro Gly Tyr Cys Cys Ser Lys Phe Gly Tyr Cys Gly Val Gly
                35                  40                  45

CGC GCC TAT TGT GGC GAT GCT GAG CAG AAG GTT GAA GAT CAT CCA TCT    251
Arg Ala Tyr Cys Gly Asp Ala Glu Gln Lys Val Glu Asp His Pro Ser
                50                  55                  60

AAT GAT GCT GAT GTT CCT GAG TTT GTT GGA GCT GGT GCC CCA            293
Asn Asp Ala Asp Val Pro Glu Phe Val Gly Ala Gly Ala Pro
                65                  70                  75
```

-continued

```
TGATGCTCGA AGCCAGGTAA TCGTAATGGC ATGGGTTACC TAATAAGTAA ACTCATTGTG      353

CCTAGCTTGC TACATGCTTA TCCACTATAA ATAAGCTCCT ACAGGAGTTG TGTTTTTCTT      413

TTAATTTTGT AATCAAGGGT TTGACTTTAA TTAATGAGAC CAATGTATAC TTGCATGTCG      473

GATAAATATN TAACTAAGCC ACTCGTATTG GTTTATTATA AAACTACTAT AAAAAAAAAA      533

AAAAAAAAAA AAAAAA                                                     550
```

(2) INFORMATION FOR SEQ ID NO:8:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:8:

```
Met Met Lys Ser Phe Val Ile Val Met Leu Val Met Ser Met Met Val
1               5                   10                  15

Ala Thr Ser Met Ala Ser Gly Glu Cys Asn Met Tyr Gly Arg Cys Pro
            20                  25                  30

Pro Gly Tyr Cys Cys Ser Lys Phe Gly Tyr Cys Gly Val Gly Arg Ala
        35                  40                  45

Tyr Cys Gly Asp Ala Glu Gln Lys Val Glu Asp His Pro Ser Asn Asp
    50                  55                  60

Ala Asp Val Pro Glu Phe Val Gly Ala Gly Ala Pro
65                  70                  75
```

(2) INFORMATION FOR SEQ ID NO:9:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:9:

```
Xaa Xaa Xaa Cys Xaa Xaa Xaa Xaa Xaa Cys Xaa Xaa Xaa Xaa Cys Cys
1               5                   10                  15

Xaa Xaa Xaa Xaa Xaa Cys Xaa Xaa Xaa Xaa Xaa Xaa Cys Xaa
            20                  25                  30
```

ANTI-MICROBIAL PROTEINS

The present invention relates to anti-microbial proteins isolatable from sugar beet.

According to the present invention there is provided anti-microbial protein comprising a peptide having the amino acid sequence: $AA_1$-$AA_2$-$AA_3$-Cys-$AA_5$-$AA_6$-$AA_7$-$AA_8$-$AA_9$-Cys-$AA_{11}$-$AA_{12}$-$AA_{13}$-$AA_{14}$-Cys-Cys-$AA_{17}$-$AA_{18}$-$AA_{19}$-$AA_{20}$-$AA_{21}$-Cys-$AA_{23}$-$AA_{24}$-$AA_{25}$-$AA_{26}$-$AA_{27}$-$AA_{28}$-Cys-$AA_{30}$, SEQ ID No.9 wherein "AA" designates any one of the commonly found 20 amino acids. It is preferred that $AA_7$ is tyr; $AA_{14}$ is tyr; and $AA_{18}$ is lys. In addition it is still more preferred that $AA_{24}$ is val; $AA_{26}$ is arg; and $AA_{27}$ is ala An anti-microbial protein includes a protein (alone or in combination with another material) which is toxic or growth inhibitory under any circumstances to any micro-organism, including bacteria, (most particularly Gram positive bacteria), viruses and particularly fungi. Such anti-microbial proteins include those that exhibit anti-microbial activity upon contact with a micro-organism and those that are anti-microbial as a consequence of assimilation or respiration thereof.

The invention also includes an anti-microbial protein having the sequence depicted in any one of SEQ ID Nos. 1–3.

The invention still further includes pure protein which is substantially similar to any one of the above mentioned proteins.

By "substantially similar" is meant pure proteins having an amino acid sequence which is at least 85% similar to the sequence of the proteins according to the invention. It is preferred that the degree of similarity is at least 90%, and still more preferred that the degree of similarity is at least 95%.

In the context of the present invention, two amino acid sequences with at least 85%, 90% or 95% similarity to each other have at least 85%, 90%, or 95% identical or conservatively replaced amino acid residues in a like position when aligned optimally allowing for up to 2 gaps with the proviso that in respect of each gap a total not more than 3 amino acid residues is affected. In the case of the proteins specifically depicted in SEQ ID Nos. 1 and 2, the number of gaps may be increased to 4 with the proviso that in respect of each gap a total of not more than 5 amino acid residues is affected.

For the purpose of the present invention conservative replacements may be made between amino acids within the following groups:

(i) Serine and Threonine;
(ii) Glutamic acid and Aspartic acid;
(iii) Arginine and Lysine;
(iv) Asparagine and Glutamine;
(v) Isoleucine, Leucine, Valine and Methionine;
(vi) Phenylalanine, Tyrosine and Tryptophan
(vii) Alanine and Glycine The invention still further includes pure proteins which are at least 90% identical to the anti- microbial proteins according to the invention, as well as pure proteins which have at least 90% of the specific activity thereof. For the purposes of the present application, specific activity is a measurement of the amount of growth or replication inhibition produced by a specified quantity of the protein on a specified quantity of a specified micro-organism.

The invention still further includes said pure proteins in combination with at least one protein selected from the group consisting of those depicted in SEQ ID Nos. 4–6.

Such combined proteins may be further combined with one or more of the known "pathogenesis-related proteins". Infection of plants with fungal or viral pathogens may induce a systemic synthesis of about 10 families of homologous pathogenesis-related proteins (PR proteins) in vegetative tissues. Such PR-proteins have been classified into 5 groups. The PR-2, PR-3 and PR-5 proteins are beta-1,3-glucanase, chitinases and thaumatin-like proteins respectively. Specific functions have not been assigned to the PR-1 and PR-4 groups of proteins. The PR-4 proteins are similar to C-terminal domains of prohevein and the putative wound-induced WIN proteins of potato, thus lacking the N-terminal hevein domain. It is particularly preferred that the proteins according to the invention are combined with one or more proteins which are the basic counter parts of the P-R 4 group of proteins, meaning the basic counter part of proteins similar to the C-terminal domains of prohevein and the putative wound-induced WIN proteins of potato. It is particularly preferred that the basic counter-part of the said pathogenesis-related proteins is a chitin-binding WIN protein, in particular that produced by barley grain or stressed barley leaves.

The invention still further includes recombinant DNA comprising a sequence encoding a protein having the amino acid sequence of the above disclosed anti-microbial proteins. In particular the DNA may encode at least one of the proteins the sequences of which are depicted in SEQ ID Nos. 1–3, optionally in addition to at least one of the proteins the sequences of which are depicted in SEQ ID Nos. 4–6. The recombinant DNA may further encode a protein having herbicide resistance, plant growth-promoting, anti-fungal, anti bacterial, anti-viral and/or anti-nematode properties. In the case that the DNA is to be introduced into a heterologous organism it may be modified to remove known mRNA instability motifs (such as AT-rich regions) and polyadenylation signals (if any are present), and/or codons which are preferred by the organism into which the recombinant DNA is to be inserted may be used so that expression of the thus modified DNA in the said organism yields substantially similar protein to that obtained by expression of the unmodified recombinant DNA in the organism in which the anti-microbial protein according to the invention is endogenous.

The invention still further includes recombinant DNA which is "similar" to that mentioned above. By "similar DNA" is meant a sequence which is complementary to a test sequence which is capable of hybridizing to the inventive recombinant sequence. When the test and inventive sequences are double stranded the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50 and 70° C. in double strength citrate buffered saline (SSC) containing 0.1%SDS followed by rinsing of the support at the same temperature but with a buffer having a reduced SSC concentration. Depending upon the degree of stringency required, and thus the degree of similarity of the sequences, such reduced concentration buffers are typically single strength SSC containing 0.1%SDS, half strength SSC containing 0.1%SDS and one tenth strength SSC containing 0.1%SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1%SDS.

The invention still further includes a DNA sequence which is complementary to one which hybridizes under stringent conditions with the recombinant DNA according to the invention.

Also included in the present invention is: a vector which contains the above disclosed DNA which is expressible in plants and linked to a plant operable promoter and terminator; plants transformed with such DNA; the progeny of such plants which contain the DNA stably incorporated and hereditable in a Mendelian manner, and/or the seeds of such plants and such progeny. The transformed plants are made by known methods and include regeneration of plant cells or protoplasts transformed with the DNA of the invention according to a variety of known methods (Agrobacterium Ti and Ri plasmids, electroporation, micro-injection, micro-projectile gun etc). The transformed cell may in suitable cases be regenerated into whole plants in which the nuclear material is stably incorporated into the genome. Both monocot and dicot plants may be obtained in this way. Examples of transformed plants according to the present invention include: fruits, including tomatoes, mangoes, peaches, apples, pears, strawberries, bananas, and melons; field cops such as canola, sunflower, tobacco, sugar beet, small grain cereals such as wheat, barley and rice, maize and cotton, and vegetables such as potato, carrot, lettuce, cabbage and onion. The preferred plants are sugar beet and maize.

The invention still further includes protein derived from expression of the said DNA, and anti-microbial protein produced by expression of the recombinant DNA within plants transformed therewith.

The invention still further includes an anti-microbial composition containing one or more of the proteins according to the invention; a process for combatting fungi which comprises exposing them to such proteins, and an extraction process for obtaining anti-microbial proteins from organic material containing them comprising submitting the material—preferably in the form of a micro-organism—to maceration and solvent extraction. It will be appreciated that the anti-microbial protein exhibits little, if any, anti-microbial effect on the micro-organism which is the source of the organic material referred to in the previous sentence.

The invention will be further apparent from the following description and the associated drawings and sequence listings.

Figure 3:
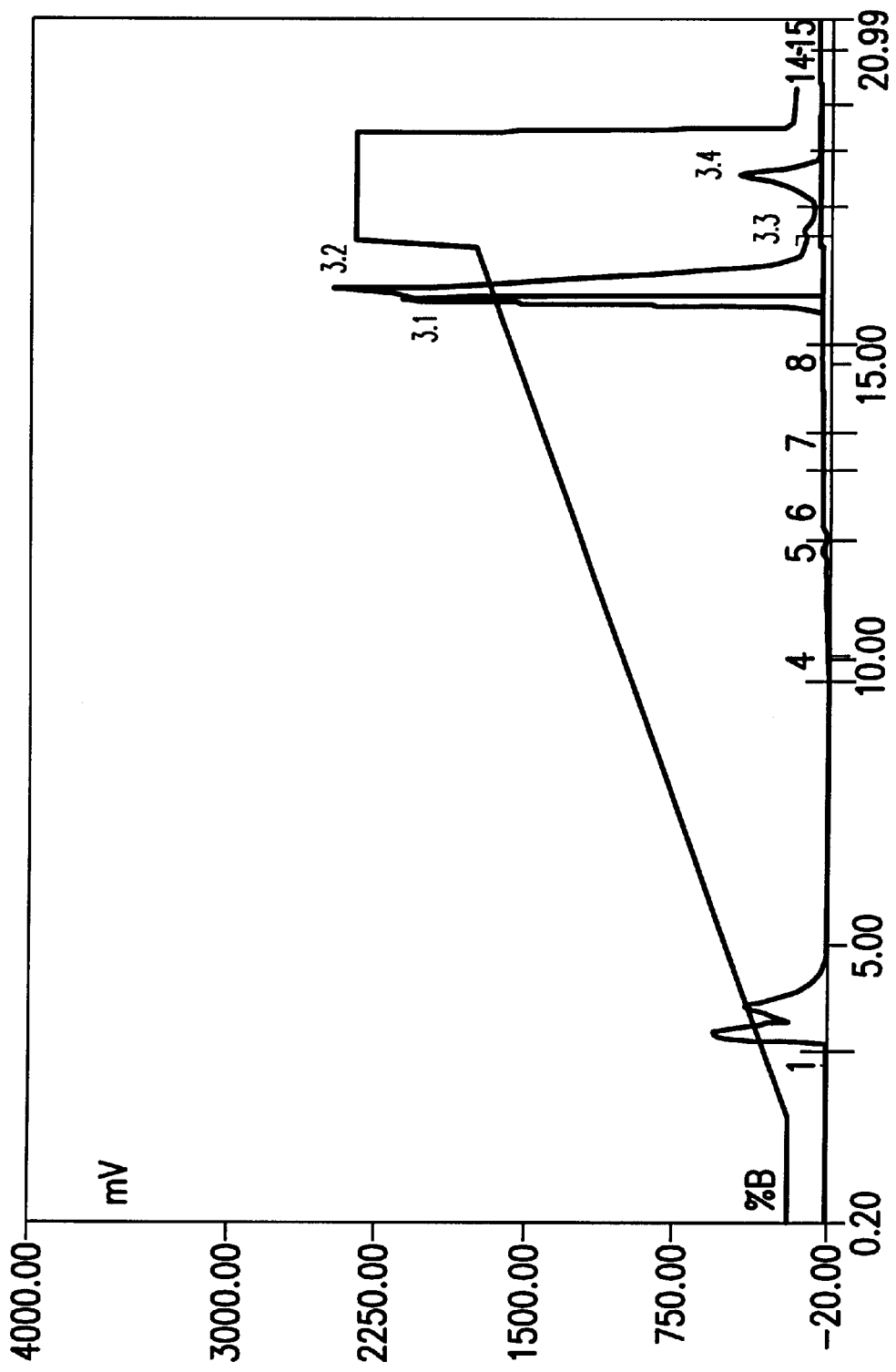
FIG. 3 shows a typical elution profile from an RP-HPLC column of the proteins represented by peak 3 in FIG. 2.

SEQ ID No. 1 shows the amino acid sequence of protein represented by peak 3.1 in FIG. 3; SEQ ID No. 2 shows the amino acid sequence of protein represented by peak 3.2 in FIG. 3; and SEQ ID No. 3 shows the amino acid sequence of protein represented by peaks 1 and 2 in FIG. 6; SEQ ID Nos. 4–6 show the amino acid sequences of three known anti-fungal proteins; SEQ ID No. 7 shows the nucleotide sequence of the cDNA encoding the protein depicted in SEQ ID No. 3; and SEQ ID No. 8 shows the translation product of the transcript encoded by the cDNA sequence depicted in SEQ ID No. 7, which product includes N- and C-terminal extensions of the protein depicted in SEQ ID No. 3.

Isolation of Intercellular Washing Fluid

IWF is isolated from 500–700 gram sugar beet leaves by submerging them in 20 mM HAc (pH 4.5). The thus submerged leaves are then placed in an exicator and vacuum infiltrated for 5 min at 4 torr (max). Following air-drying of the leaf surface, the IWF is collected by centrifugation at 500 g for 15 min in 500 ml centrifuge tubes.

Cation exchange chromatography

The thus obtained IWF is fractionated by cation exchange chromatography on a 10 ml CM-Sepharose column (Pharmacia LKB) pre-equilibrated in starting buffer (20 mM HAc (pH 4.5)). The fractionation is performed at 4° C. at a flow rate of 25 ml/h. Fractions of 3 ml are collected. Proteins not bound to the column are removed by extensive washing of the column with starting buffer. Bound proteins are eluted by applying to the column further starting buffer comprising stepwise increased salt concentrations: viz, 0.1 M NaCl, 0.3 M NACl and 0.5 M NaCl. The absorbance at 280 nm of the eluate is measured, and fractions judged to comprise protein are tested for their anti-fungal activity against *C. beticola* using the microtiter plate bioassay described previously (PCT Patent Application No. PCT/DK92/00108, Publication No. WO 92/17591, now assigned to Sandoz LTD).

Figure 1:
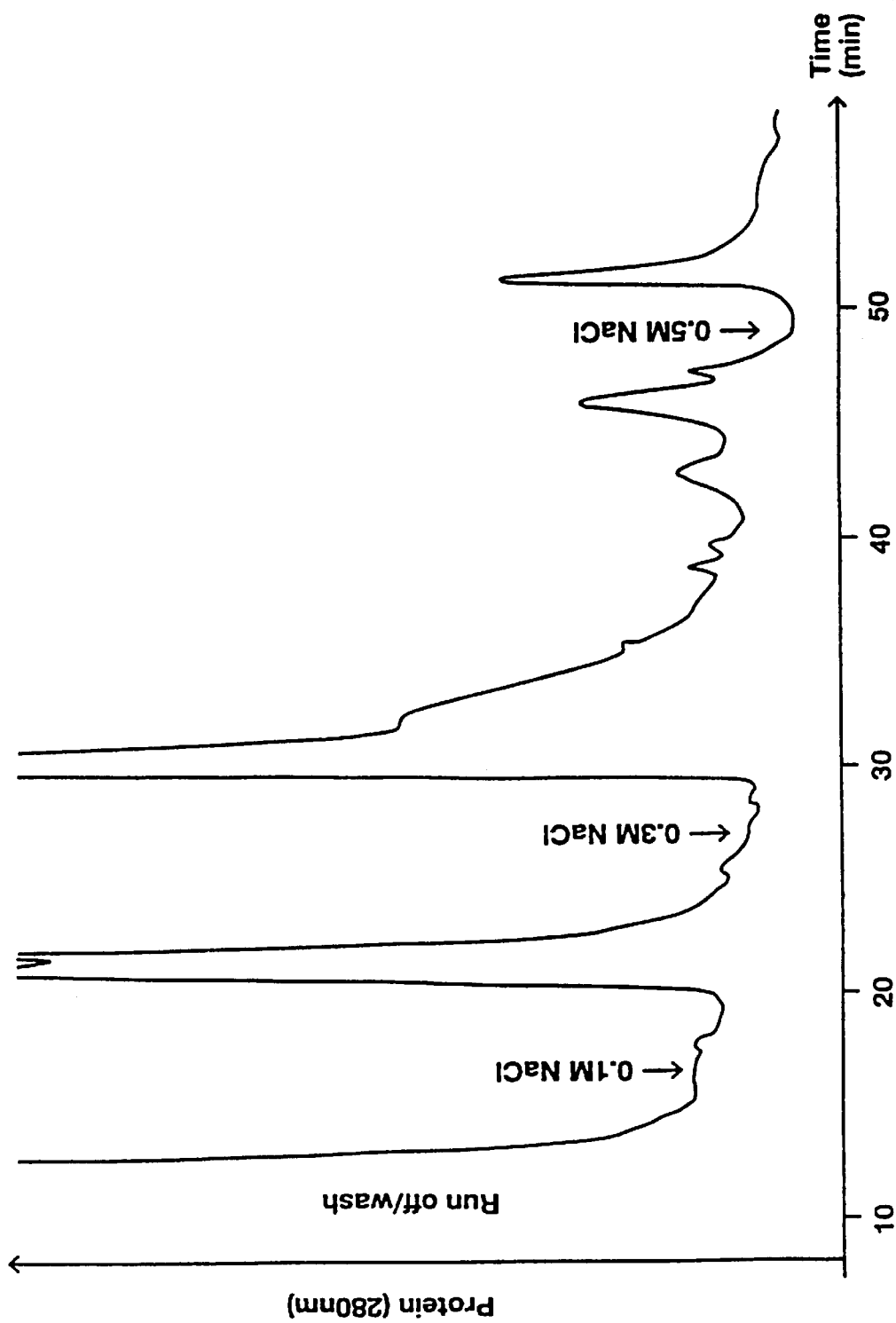
FIG. 1 shows a typical elution profile of intercellular washing fluid from a CM-Sepharose column.

A typical elution profile is shown in FIG. 1. The eluates resulting from application to the column of starting buffer comprising the 0.3M NaCl and 0.1M NaCl are further purified as described below.

Purification of antifungal Proteins in the 0.3 M NaCl eluate from the CM-Sepharose. FPLC Chromatography The 0.3M NaCl protein fraction is desalted by overnight dialysis (MW cut off: 3 kDa) against 20 mM HAc (pH 4.5) at 4° C. Betaine is added at a concentration of 5% (w/v) to the thus dialysed protein fraction. Four ml of the resulting solution is then fractionated by cation exchange fast protein liquid chromatography (FPLC) using a Mono S HR 5/5 column (Pharmacia LKB) equilibrated in 20 mM HAc (pH 4.5) containing 5% (w/v) betaine (A-buffer). Bound proteins are eluted with a linear salt gradient from 0 to 0.3 M NaCl in 30 ml of the A-buffer followed by a step elution with 1.0 M NaCl in the same buffer. Flow rate is 1 ml/min.

Figure 2:
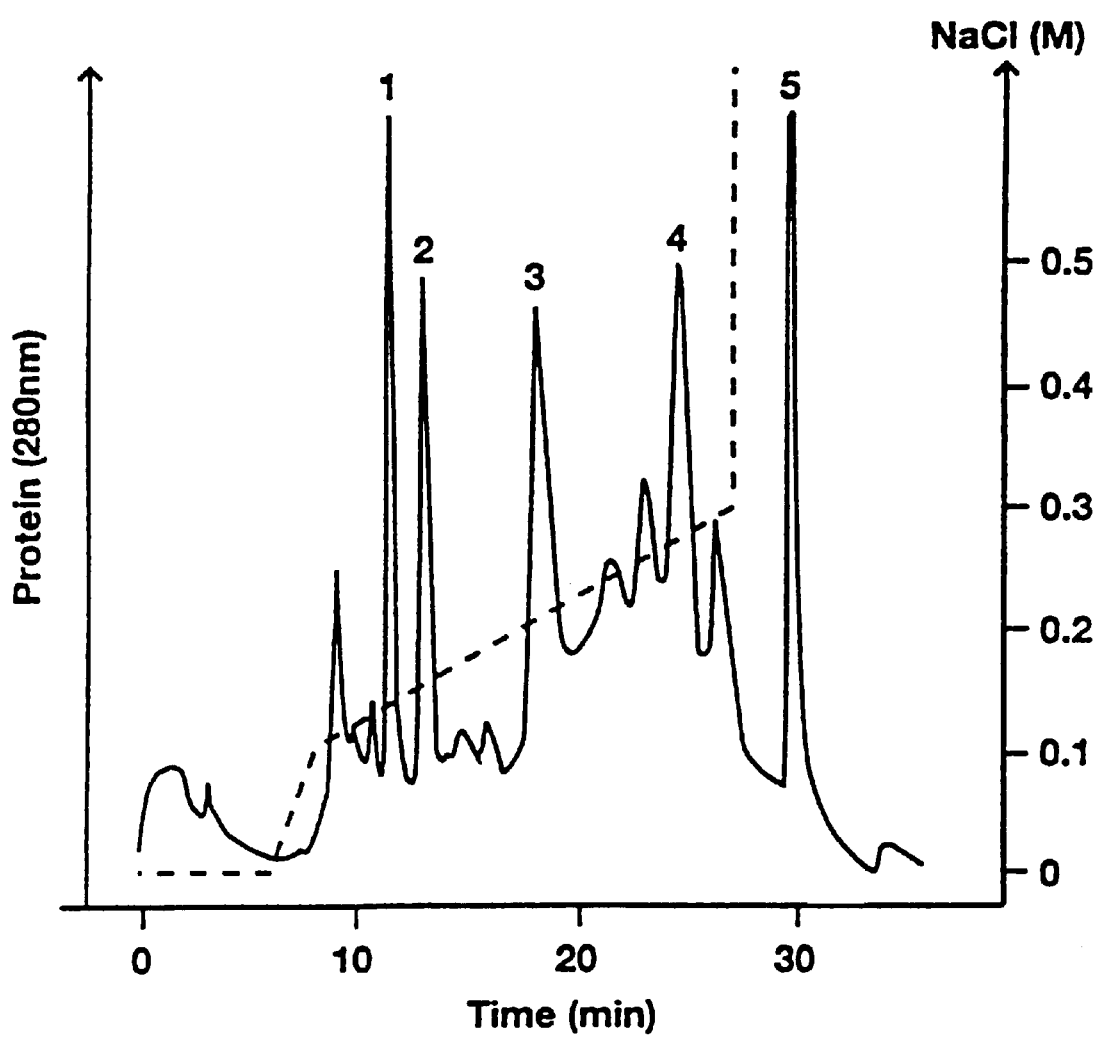
FIG. 2 shows a typical elution profile from a Mono S FPLC column of the 0.3M NaCl fraction shown in FIG. 1.

FIG. 2 shows that the 0.3M NaCl fraction contains a number of distinct proteins, the quantitatively most significant of which are designated as peaks 1–5. When separated by SDS-PAGE using the Phast System (Pharmacia LKB), silver stained 10–15% gradient Phast gels or High Density gels (Pharmacia LKB) reveal that each of the peaks 1–5 contains 2–5 protein bands.

Reverse Phase HPLC

Protein peak 3 (depicted in FIG. 2) from the Mono S column is further purified by reverse phase (RP-) HPLC on a Vydac $C_4$ silica column (The Separations Group, CA, USA). The solvent system is A: 0.1% TFA in water and B: 0.1% TFA in acetonitrile. Proteins are eluted with a linear gradient of 5 to 45% of the B-buffer applied in 18 min after sample loading followed by 60% B-buffer in 2 min. Flow rate is 0.7 ml/min. Protein is detected by monitoring the absorbance of the eluate at 214 and 280 nm. Discrete protein peaks are collected and lyophilized. The thus lyophilized proteins are washed twice with water, re-lyophilized and subsequently resolved in 10 mM Tris-HCl (pH 8.0), prior to analysis of purity and anti-fungal activity.

FIG. 3 shows that peak 3 from FIG. 2 is separated into four peaks (designated as 3.1–3.4 in FIG. 3) on the RP column. SDS-PAGE of peaks 3.1–3.4 reveals that each is composed of pure proteins having a molecular weight of about 7 kDa (peaks 3.1, 3.2 and 3.3) and 2.5–3 kD (3.4). Purification of antifungal Proteins in the 0.1 M NaCl eluate from the CM-Sepharose.

Figure 5:
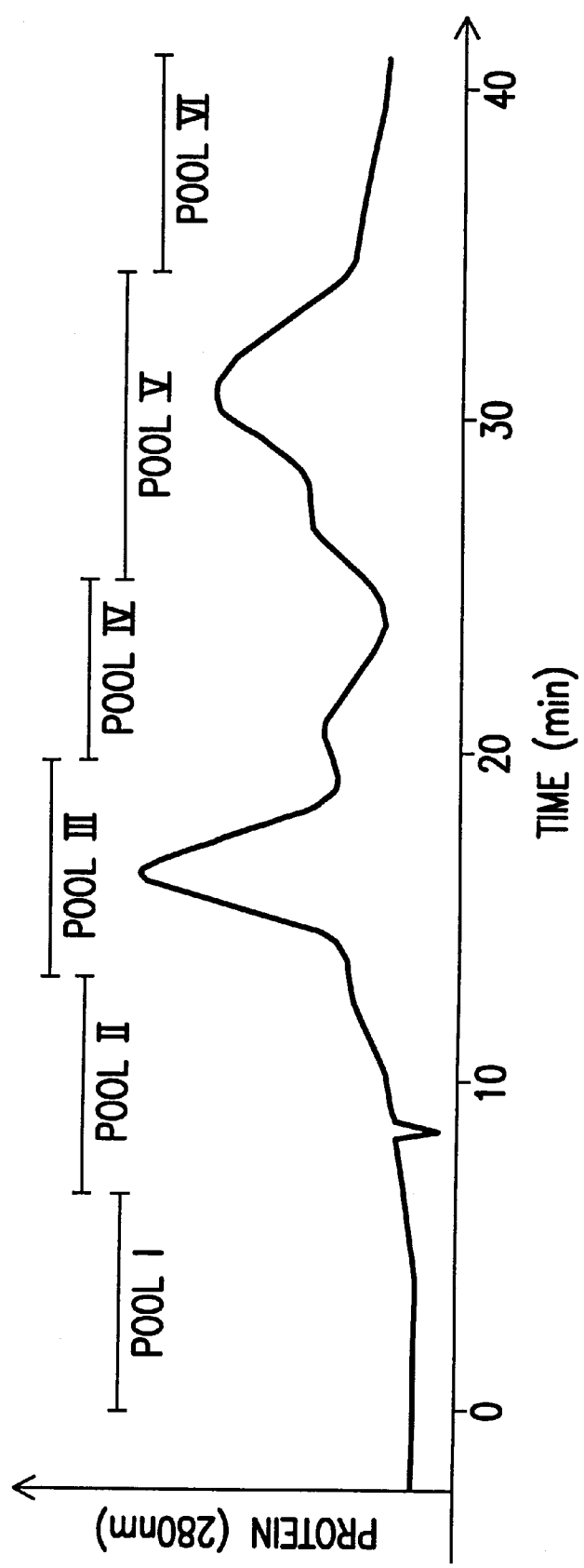
FIG. 5 shows a Sephadex G75 gel filtration chromatogram of the 0.1M fraction depicted in FIG. 1.

Five ml of the 0.1 M NaCl eluate from FIG. 1 is fractionated by gel filtration on a 370 ml Sephadex G-75 column (Pharmacia LKB) equilibrated in 50 mM MES (pH 6.0) at a flow rate of 20 ml/hour. Fractions of 10 ml are collected. Such fractions are subsequently pooled in six larger fractions, I–VI, containing approximately 50 ml each (FIG. 5).

Cation exchange (Mono S)

Figure 6:
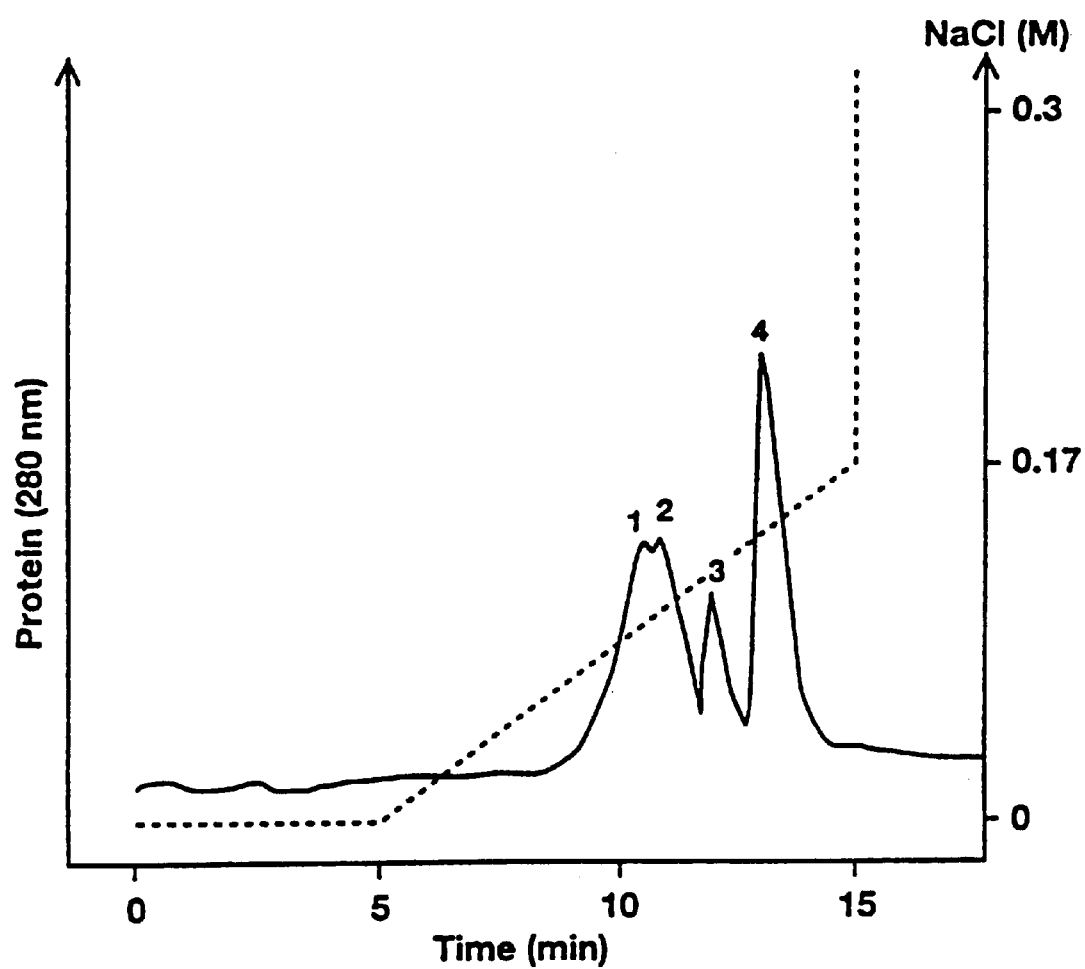
FIG. 6 shows a typical elution profile from a Mono S FPLC column of peak (pool) V depicted in FIG. 5.

Pool V (shown in FIG. 5) from the Sephadex G-75 column is loaded onto a Mono S FPLC column equilibrated in buffer A: 50 mM MES (pH 6.0), containing 5% betaine (w/v). After washing with the A-buffer, bound proteins are eluted at a flow rate of 1 ml/min with a linear gradient from 0 to 0.5 M NaCl in 30 ml of the A-buffer (FIG. 6). When protein represented by peaks 1 and 2 is subjected to SDS gel electrophoresis in the presence of DTT two distinct bands are observed. The first band has a molecular weight of between 2.5 and 3 kDa, and the second band, which represents an unreduced dimer of the protein of the first band, has a molecular weight of about 5 kDa.

Identification of Antifungal Proteins
Antifungal activity

Figure 4:
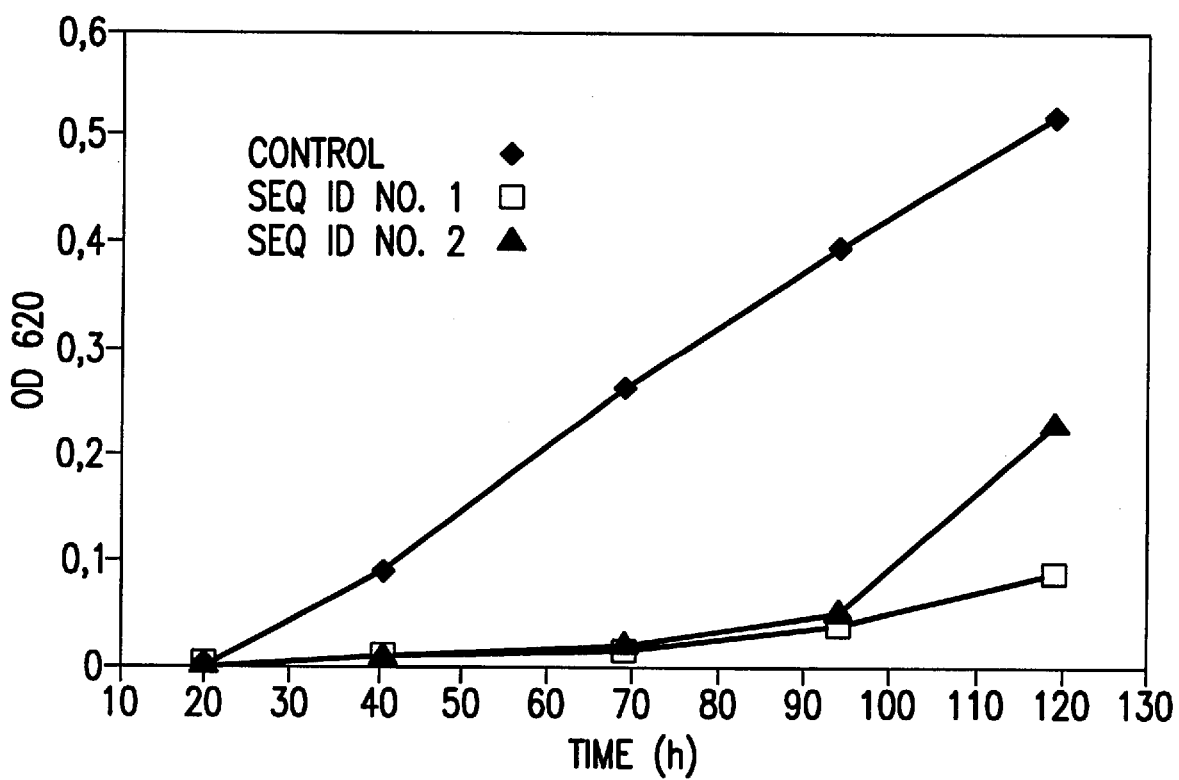
FIG. 4 shows the anti-fungal activity of 10 ug of the protein represented by peaks 3.1 and 3.2 in FIG. 3 (SEQ ID Nos. 1 and 2 respectively)
Figure 7:
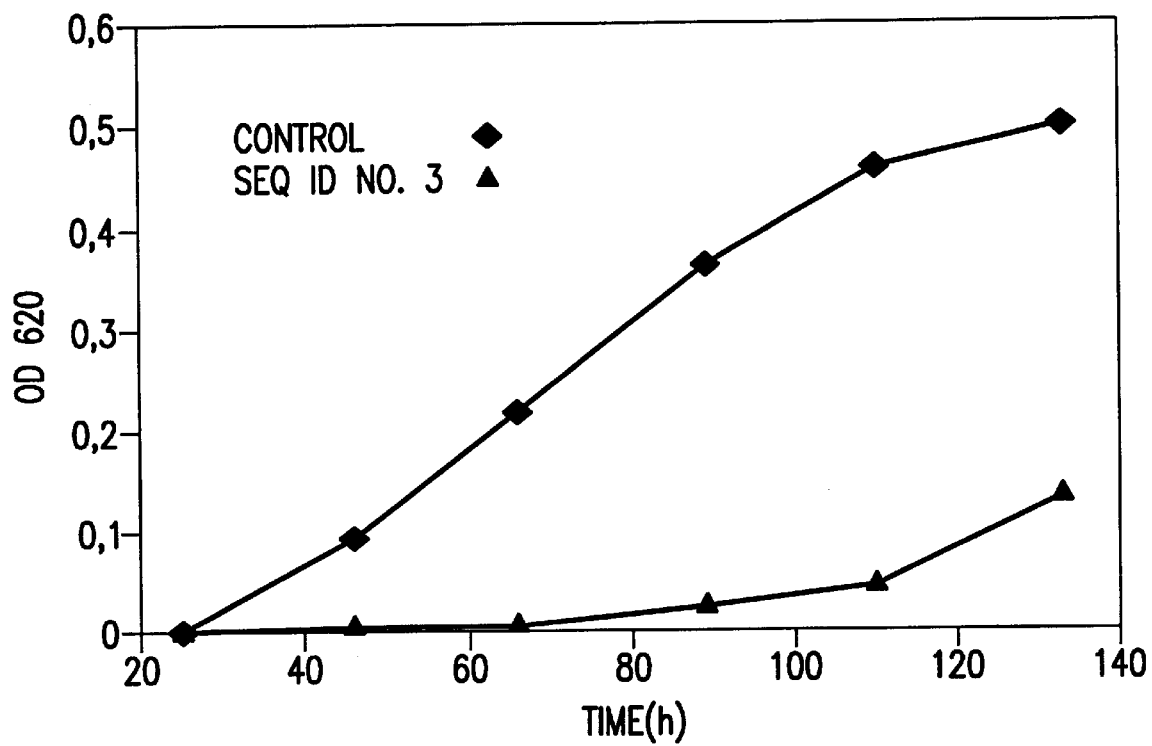
FIG. 7 shows the anti-fungal activity of 10 ug of the protein depicted in peaks 1 and 2 (SEQ ID No. 3) in FIG. 6.
Figure 8A:
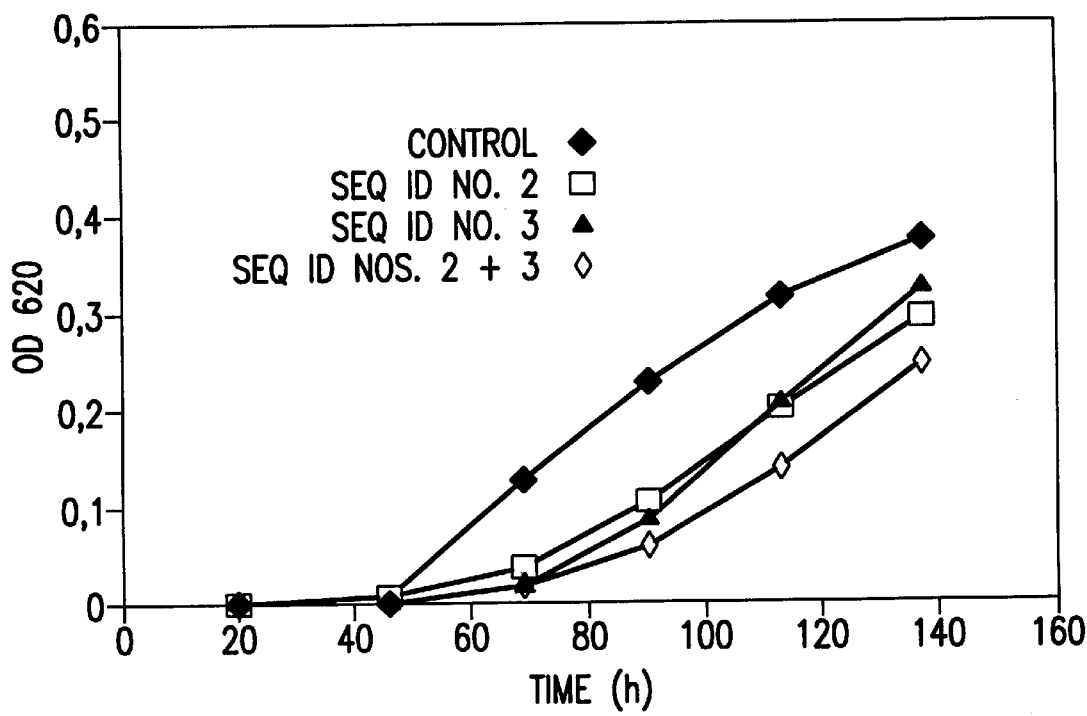
FIG. 8A shows the combined anti-fungal activity of 2 ug of each the proteins represented by SEQ ID Nos 2 and 3.
Figure 8B:
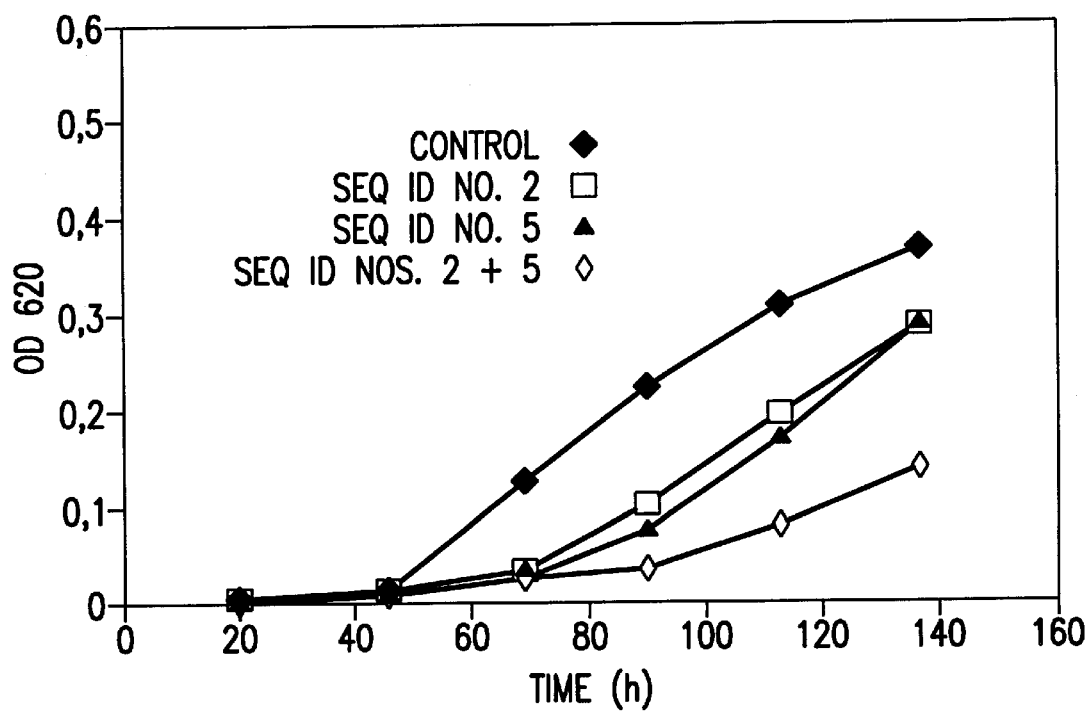
FIG. 8B shows the combined anti-microbial activity of 2 ug of each of the proteins represented by SEQ ID Nos 2 and 5.

FIGS. 4, and 7–8 show that the proteins represented by peaks 3.1 and 3.2 (SEQ ID Nos 1 and 2 respectively) in FIG. 3 and peaks 1 and 2 (SED ID No 3) in FIG. 6 have significant anti-fungal activity, inter alia, against *C. beticola*. The inhibition of fungal growth is measured in 96 well micro-titre plates at 620 nm, essentially as described in WO 92/17591. *C. beticola* treated with such protein possess stunted hyphae which are thickened and more branched when compared to those of fungus grown in the absence of the anti-microbial proteins (FIGS. 8A, 8B).

The proteins, either alone or in combination with WIN N (which is purified from barley grain or stressed barley leaf as described by Hejgaard et al (FEBS Letters, 307, 389–392 (1992)), and/or a protein having a sequence corresponding to at least one of those given in SEQ ID Nos. 4–6, are incubated with spores of *C. beticola*. The assay mix (240 ul) contains 100 ul of potato dextrose broth (Difco), 40 ul protein sample (or buffer control) in 100 mM Tris and 20 mM NaCl (pH 8.0) as well as approximately 400 spores in 100 ul water. The micro-titre plates are sealed with tape to avoid evaporation and contamination and subsequently incubated at room temperature on an agitator operated at 200 rpm. The absorbance at 620 nm is measured each day for 8 days and plotted for each concentration of protein vs time.

Amino acid sequencing

The purified antifungal proteins corresponding to peaks 3.1 and 3.2 in FIG. 3 (SEQ ID Nos 1 and 2 respectively) which originate from the 0.3 M NaCl eluate from the CM-Sepharose column, (FIG. 1); and protein corresponding to peaks 1 and 2 in FIG. 6 (SEQ ID No 3) which originates from the 0. 1M NaCl eluate from the said CM-Sepharose column are carboxymethylated and subjected to RP-HPLC on a Vydac $C_4$ column. The solvent system is A: 0.1% TFA in water and B: 0.1% TFA in acetonitrile. The proteins elute as single peaks with slightly different retention times. The C-terminal sequences of the proteins is obtained by cleavage thereof with endo-R-proteinase and subsequent purification by RP-HPLC on a Vydac $C_{18}$ column.

Production of transformed plants

The genes encoding proteins according to the invention are introduced into plants. Based on gene specific primers, the coding regions of the genes encoding the proteins are synthesized from corresponding mRNA using PCR. After addition of promoter and terminator sequences, the genes encoding the said proteins are introduced into a plant transformation vector. The vector may optionally include a gene encoding a WIN protein, such as that obtained from stressed barley leaf or barley grain, and/or a gene encoding a protein depicted in SEQ ID No. 4, SEQ ID No. 5 and/or SEQ ID No. 6, and/or a gene encoding a chitinase and or a glucanase. The preferred chitinase is the chitinase 4 described in PCT Patent Application No. PCT/DK92/00108 (Publication No. WO 92/17591). Agrobacterium tumefaciens, for example, may be transformed with these vectors. Plant cells are then treated with such transformed Agrobacterium, and the thus transformed plant cells are regenerated into whole plants, in which the new nuclear material is stably incorporated into the genome. It will be appreciated, however, that the DNA encoding a protein according to the present invention, (or combination of such proteins), optionally further encoding other proteins, may be introduced into plant cells by other known methods, including use of a micro-projectile gun, electroporation, electro-transformation, and micro-injection etc, and that regeneration of transformed plant cells is carried out according to methods known to the skilled man, including treatment of the cells with cytokines where this is necessary or desirable in order to improve the regeneration frequency.

Moreover, suitable micro-organisms (i.e. those in which the production of the present inventive proteins is not substantially toxic) may be transformed with a vector comprising the gene (or genes) encoding the protein so that the transformed micro-organisms produce such protein. The micro-organisms may further comprise the genes encoding other proteins, such as a WIN protein and/or a protein the sequence of which is depicted in one or more of SEQ IDs No. 4–6. Furthermore, such other proteins may further comprise various chitinases and/or glucanases. A particularly preferred such other protein is the chitinase 4 as described in PCT Patent Application No. PCT/DK92/00108 (Publication No. WO 92/17591).

These micro-organisms may then be used to combat plant pathogens. For example the transformed micro-organisms may be dried and sprayed onto infected plants or plants at risk of infection.

We claim:

1. A purified protein having the sequence depicted in any one of SEQ ID Nos 1–3.

2. The protein according to claim 1, in combinations with at least one protein selected from the group consisting of those depicted in Seq. ID Nos. 4–6.

3. The protein according to claim 1, in combination with at least one further protein having herbicidal resistance, plant growth-promoting, anti-fungal, anti-bacterial, anti-viral and/or anti-nematode properties.

4. The protein derived from expression of DNA encoding a protein as claimed in claim 1.

5. An anti-microbial composition comprising one or more of the proteins as claimed in claim 1.

6. A process for combating fungi which comprises exposing the fungi to at least one protein claimed in claim 1.

7. An extraction process for obtaining anti-microbial proteins as claimed in claim 1, from organic material containing them comprising submitting the material to maceration and solvent extraction, characterized in that material is a microorganism or a plant.

8. A composition comprising the protein combination of claim 2.

9. A composition comprising the protein combination of claim 3.

10. A process for combating fungi comprising exposing the fungi to the protein combination of claim 2.

11. A process for combating fungi comprising exposing the fungi to the protein combination of claim 3.

12. The process of claim 6 further comprising exposing the fungi to at least two proteins having a sequence depicted in any one of SEQ ID Nos 1–3.

\* \* \* \* \*